United States Patent [19]

Jones

[11] 4,154,248
[45] May 15, 1979

[54] BODY IMPLANTABLE ELECTRICAL STIMULATOR

[75] Inventor: Richard A. Jones, Columbia Heights, Minn.

[73] Assignee: Medtronic, Inc., Minneapolis, Minn.

[21] Appl. No.: 793,642

[22] Filed: May 4, 1977

[51] Int. Cl.² ............................................. A61N 1/36
[52] U.S. Cl. ............................................... 128/419 P
[58] Field of Search ....... 128/419 P, 419 PG, 419 PS, 128/419 C, 410 F, 419 R, 421, 422, 423

[56] References Cited
U.S. PATENT DOCUMENTS 3,908,668  9/1975  Bolduc ............................ 128/419 P Primary Examiner—William E. Kamm
Attorney, Agent, or Firm—Wayne A. Sivertson

[57] ABSTRACT

A body implantable electrical stimulator of the type having a separable lead and signal generator. The signal generator includes a jack for accepting a portion of the lead to secure it to the generator. In a preferred embodiment, the lead is provided with a pin and the jack includes a terminal for engagement with the pin, the jack further including a viewing port which facilitates the viewing of the engagement of the pin and terminal. The viewing port may include a magnifying member so as to provide a magnified image of the nature of the engagement between the pin and jack.

7 Claims, 4 Drawing Figures

U.S. Patent May 15, 1979 4,154,248
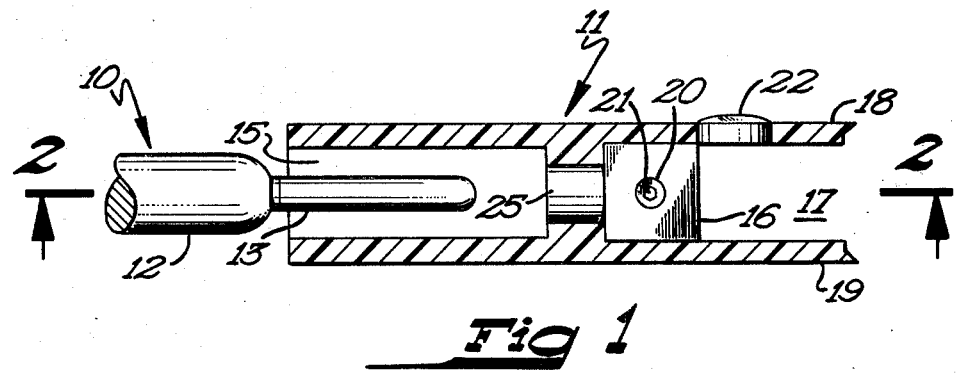
Fig 1
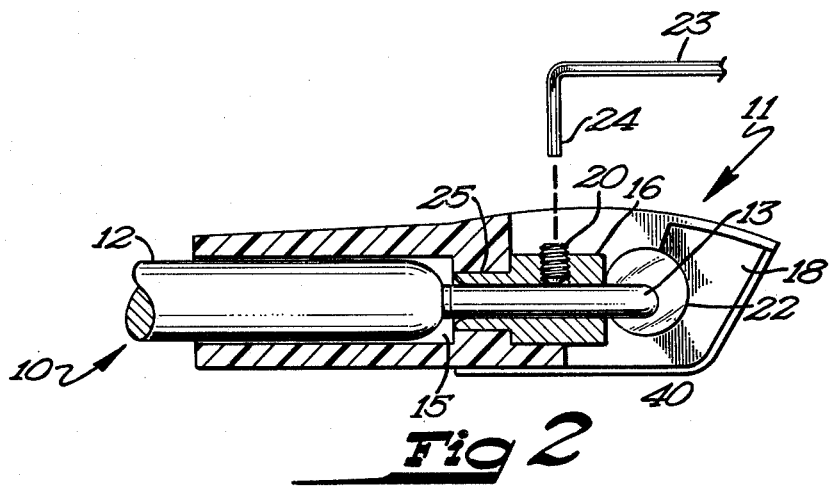
Fig 2
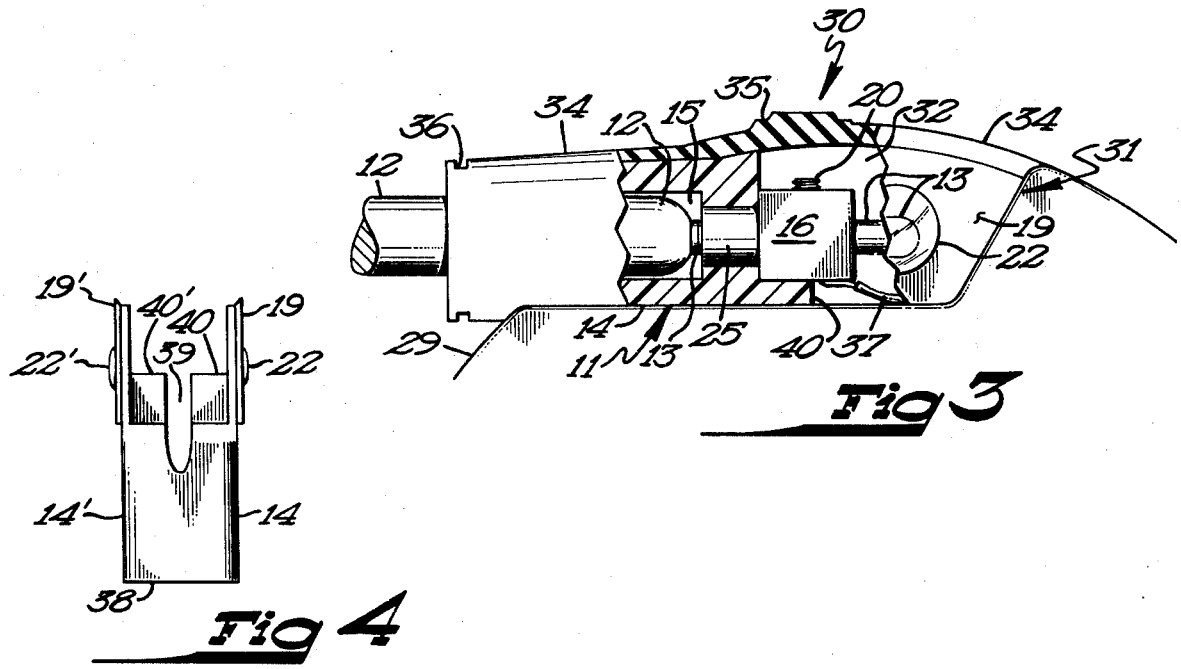
Fig 3
Fig 4

BODY IMPLANTABLE ELECTRICAL STIMULATOR

BACKGROUND OF THE INVENTION

Body implantable electrical stimulators are well known to the prior art, the most common being the cardiac pacemaker. Typically, such stimulators are formed of a separable lead and signal generator with provision being made to electrically and mechanically interconnect the lead and generator to complete the stimulator unit.

Prior art signal generators have been formed by molding their components, including the mechanical and electrical connectors for the lead, in a matrix of encapsulating material which supports the components and shields them from the body environment. Typically, the encapsulating material is an epoxy which is clear and allows a viewing of the interconnection between the lead and generator.

More recently, the electrical components forming the signal generator have been housed within a rigid enclosure formed of a plurality of preformed members which are typically welded together to complete the enclosure. The interconnection between the generator and the lead, when it is desired that these members be separable, occurs outside of such an enclosure. While it is possible to mold the interconnect assembly from epoxy, such a process diminishes one of the benefits from the use of a preformed enclosure—elimination of the epoxy encapsulation process. Thus, a preformed interconnect assembly, formed by injection molding, for example, which may be reliably secured to a preformed enclosure housing the generator components would greatly facilitate assembly of the stimulator. The amount of handling would be reduced with the remaining handling being easier to perform than an epoxy molding process. However, available materials for injection molding which are also suitable for use within the body environment are opaque, thus preventing the viewing of the interconnection between the lead and generator that is possible in a molded epoxy.

SUMMARY OF THE INVENTION

The present invention allows the use of a preformed interconnect assembly for a lead and signal generator while providing a view of the interconnection between the lead and generator. The assembly may be formed by injection molding and result in an opaque assembly and still maintain the viewing of the interconnection. In a preferred embodiment, the lead is provided with a pin and the interconnect assembly is formed as a jack secured to the signal generator. The jack is provided with a terminal having a bore therethrough with the pin being insertable through the bore from one end to extend from the other. A viewing port is provided adjacent the bore of view the extension of the pin from the bore and terminal thereby assuring that the pin occupies the entirety of the bore. That is, the extension of the pin from the bore indicates maximum mechanical interaction between the pin and the terminal. The pin may be secured within the bore in any known manner, as by a set screw, for example. The viewing port may be provided with a magnifying member to enhance the viewing of the engagement between the pin and terminal.

BRIEF DESCRIPTION OF THE DRAWINGS

FIG. 1 is a top view in partial cross-section illustrating the concept of the present invention as viewed along the line 1—1 in FIG. 2.

FIG. 2 is a side view in partial cross-section illustrating the concept of the present invention as viewed along the line 2—2 in FIG. 1.

FIG. 3 illustrates a partial cutaway of a preferred embodiment of the present invention.

FIG. 4 illustrates a top view of a preferred embodiment of the present invention.

DETAILED DESCRIPTION OF THE DRAWINGS

FIG. 1 is an exploded partial cross-section illustrating the cooperation between a lead 10 and the interconnect assembly 11 of the present invention. The body 12 of lead 10 houses and insulates an electrical conductor (not shown) which conducts the electrical signal produced by the signal generator to a distant electrode in known manner. Extending from the end of the lead body 12 is a pin 13 in electrical communcation with the conductor within the lead body 12, also in known manner. The interconnect assembly 11 has a sleeve portion 14 having an inner bore 15 of a size which will permit insertion of the pin 13 and body 12 of lead 10. Generally, the bore 15 of sleeve 14 conforms in cross-section to the body of lead 10. Alternatively, the body 12 of lead 10 may be provided with sealing rings, in known manner, in which case the bore 15 will conform to the sealing rings.

A terminal member 16 is supported on a platform within the interconnect assembly 11 adjacent the bore 15. The terminal member 16 has a bore which runs from the bore 15 through the terminal member 16 to a cavity 17 defined by side walls 18 and 19. The terminal 16 is provided with a set screw 20 accessible from its upper surface, the set screw 20 having an irregular recess 21 which is adapted to cooperate with a tool, in known manner. The set screw 20 is threadedly engaged within the terminal 16 in a manner known to the prior art, and enters or withdraws from the bore through the terminal 16 on rotation imparted to the set screw 20 via the cooperation of an appropriate tool with the irregular recess 21. In a preferred embodiment, the irregular recess 21 is hexagonal in shape and is adapted to cooperate with the tool having a hexagonal cross-section.

The bore through the terminal 16 is configured to accept the pin 13. With the pin 13 in the terminal 16, set screw 20 is turned so as to engage the pin 13 and mechanically secure it within terminal 16. A secure mechanical connection between the pin 13 and set screw 20 requires an insertion of the pin 13 within the terminal 16 to a depth such that the set screw 20 fully engages the pin 13. Further, the electrical connection between the lead 12 and a signal generator is typically accomplished through electrical communcation between the terminal 16 and pin 13. Thus, the nature of the engagement between set screw 20 and pin 13 is critical for both mechanical and electrical considerations.

One manner in which the adequacy of the penetration of the pin 13 in the bore in the terminal 16 can be established is to make the pin 13 sufficiently long to pass through the bore and extend from the terminal 16 into the cavity 17. When the pin extension in cavity 17 is seen, it is known that the proper contact can be made by set screw 20 to secure the pin 13 within the bore of terminal 16.

Depending on the process by which the interconnect assembly 11 is formed, the requirements of the body environment may dictate the use of a material which obscures the view of the extension of the pin 13 into the cavity 17. For example, one available material by which the interconnect assembly 11 may be injection molded is sold under the trademark NORYL and results in an opaque assembly. Other materials to be available in the future may be similarly opaque or at least intransparent to some degree so as to block or obscure the view of the pin 13 within the cavity 17. Thus, to assure the proper engagement between the set screw 20 and pin 13, some provision must be made for viewing of the extension of the pin 13 into the cavity 17. In the present invention, this is accomplished by providing a viewing port within one of the cavity side walls 18 or 19. As illustrated in FIG. 1, the side wall 18 is provided with a viewing port which is filled with a transparent member 22. The transparent member 22 allows a viewing of the pin 13 extension into the cavity 17 as a result of its transparency and its position adjacent the terminal 16. When an extension of the pin 13 is viewed through the member 22, it is known that the pin 13 is properly positioned for engagement by the set screw 20. In a preferred embodiment, viewing port member 22 is provided with a spherical or other magnifying surface to provide a magnified image of the extension of the pin 13 from the terminal 16. The member 22 may be secured within the viewing port in any known manner, a interference fit, for example.

FIG. 2 illustrates a cross-section of the member of FIG. 1 taken along the line 2—2 with the pin 13 extending through the bore in the terminal 16 and the lead body 12 lying within the bore 15. In FIG. 2, it can be seen that the extension of the pin 13 from the terminal 16 positions the pin 13 directly in view of the viewing port so as to facilitate the viewing of the pin 13 through the side wall 18. In this manner, the nature of the cooperation between the pin 13 and terminal 16 may be viewed so as to determine the degree of insertion of the pin 13 in the terminal 16 bore. In FIG. 2, a tool 23 is illustrated having a working end 24 which is adapted to be inserted within the irregular recess 21 of set screw 20 and cause the set screw 20 to rotate on rotation of the tool 23. The nature of the cooperation between the tool 23 and set screw 21 is known to the prior art. As illustrated, the terminal 16 is provided with a main body which rests on a platform 40 and an extending portion 25 through which the bore extends. Extending portion 25 may have a circular configuration adapted to cooperate with a similarly configured recess extending from the bore 15 so as to secure the terminal 16 to the interconnect assembly 11 as by an interference fit, for example. Alternatively, the terminal 16 and/or its extension 25 may be secured to the interconnect assembly 11 by suitable adhesive material.

Referring now to FIG. 3, there is shown a partial cut-away of a preferred embodiment of the present invention including a preferred preformed enclosure member 29. Enclosure member 29 is that shown in FIGS. 5-7 of United States Patent Application Ser. No. 659,650, filed Feb. 20, 1976, now U.S. Pat. No. 4,057,068 which is commonly owned with the present application and which is hereby incorporated by reference. With reference to the incorporated patent, the enclosure member 29 includes platform members 30 and 31 whose locations are indicated generally at 30 and 31 in FIG. 3 and a web 32 extending from the platform members 30 and 31 to maintain a circular cross-section in the terminus of the side wall of the member 29. The presence of the web allows the elimination of the cavity wall 18 with the viewing port being in cavity wall 19, in the embodiment illustrated in FIG. 3.

The interconnect assembly is placed on the platform 30 with the side wall 19 being configured to conform to the platform 31. Interconnect assembly 11 may be secured to the enclosure member 19 by an epoxy which may also partially fill the cavity formed in the embodiment of FIG. 3 by the cavity side wall 19 and the web 32, recognizing that the pin 13 must extend into the cavity. A boot 34 having a grommet 35 may then be placed over the interconnect assembly 11 to cushion any sharp edges on the interconnect assembly 11 and to provide relief for the lead. The boot 34 may be made of silicon rubber and may be maintained in position by cementing, in known fashion. Provision may also be made to seal the lead entrance as by a suture within the recess indicated at 36 in FIG. 3. The grommet 35 may either be unitary with the boot 34 or separate therefrom dependent on whether or not a difference in durometer between the boot and grommet is desirable. The grommet provides access to the set screw 20 by first being pierced with a sharp instrument to provide a path for the tool 23 while maintaining a seal on withdrawal of the tool. The member 22 illustrated in FIG. 3 provides a magnified view of the pin 13 within the cavity 17.

FIG. 3 illustrates a wire 37 welded to the terminal 16 the other end of which is connected to the feedthrough 16 illustrated in the incorporated patent to provide an electrical communication between the terminal 16 and signal generator within the enclosure member 29. Thus, on mechanical engagement between the pin 13 and terminal 16, electrical communication is also attained between the conductor within the lead body 12 and the signal generator. Any other known method of attaining electrical communication between the pin 13 and the signal generator may also be employed.

It is sometimes necessary or desirable to form an enclosure of two members such as that illustrated in FIGS. 5-7 of the incorporated patent.

FIG. 4 illustrates a top view of a preferred embodiment of an interconnect assembly suitable for such an enclosure. Essentially, the interconnect assembly of FIG. 4 provides for two leads, each associated with a different one of the enclosure members. The right-hand portion of the embodiment of FIG. 4 is as illustrated in FIG. 3 having a cavity wall 19, a viewing port and viewing port member 22, and sleeve portion 14, the cavity for the right-hand portion being completed by the web 32. Similarly, the left-hand portion has a cavity wall 19', a viewing port member 22', and a sleeve portion 14'. The sleeves 14 and 14' are joined at a web 38 having a recess 39 to accomodate the circular side wall termini of the members 29 forming the enclosure. Platforms 40 and 40' are provided for terminals such as 16 illustrated in FIGS. 1-3.

Obviously, many modifications and variations of the present invention are possible in view of the above teachings. For example, the interconnect assembly of the present invention may be adapted to the configuration of any signal generator enclosure while maintaining the viewing port to facilitate the viewing of the nature of the engagement between the pin 13 and terminal 16. Accordingly, within the scope of the appended claims, the invention may be practiced otherwise than as specifically described.

What is claimed is:

1. In a body implantable electrical stimulator of the type having separable lead means and signal generator means, the lead means including pin means and the generator means including jack means for accepting at least said pin means, the improvement wherein said jack means is preformed of an intransparent material and secured to the surface of said signal generator means, said jack means further comprising viewing port means for facilitating the viewing of the degree of acceptance of said pin means within said jack means.

2. The stimulator of claim 1 wherein said viewing facilitating means comprises magnifying means.

3. The stimulator of claim 2 wherein said viewing facilitating means provides a magnified view of the degree of insertion of said pin means through said terminal means.

4. The stimulator of claim 3 further comprising means for securing said pin means to said terminal means.

5. The stimulator of claim 1 wherein said jack means includes terminal means, said pin means being insertable through said terminal means and said viewing facilitating means providing a view of the degree of insertion of said pin means through said terminal means.

6. In a body implantable electrical stimulator of the type having separable lead means and signal generator means, the lead means including pin means and the generator means including jack means for accepting at least said pin means, the jack means comprising terminal means for engaging said pin means, the improvement wherein said jack means is formed of an intransparent material and further comprises viewing port means within said intransparent material and adjacent said terminal means for facilitating the viewing of the engagement of said pin means and said terminal means.

7. The stimulator of claim 6 wherein said viewing facilitating means comprises magnifying means.

* * * * *